United States Patent [19]
Woodcock et al.

[11] 4,155,125
[45] May 22, 1979

[54] IRIS CLIP ANCHORING MEANS FOR INTRAOCULAR LENSES

[75] Inventors: Richard F. Woodcock, South Woodstock, Conn.; William Richards, Medway, Mass.

[73] Assignee: American Optical Corporation, Southbridge, Mass.

[21] Appl. No.: 869,192

[22] Filed: Jan. 13, 1978

[51] Int. Cl.² ........................... A61F 1/16; A61F 1/24
[52] U.S. Cl. ........................................... 3/13; 16/108; 140/76
[58] Field of Search ................... 3/13; 128/335.5, 339; 16/108, 109; 140/76

[56] References Cited

U.S. PATENT DOCUMENTS

| | | | |
|---|---|---|---|
| 1,757,129 | 5/1930 | McClure | 128/339 |
| 1,960,117 | 5/1934 | Lydeard | 128/335.5 X |
| 2,311,427 | 2/1943 | Winkelmeyer | 16/108 |
| 3,996,626 | 12/1976 | Richards et al. | 3/13 |
| 4,012,823 | 3/1977 | Richards | 3/13 |

*Primary Examiner*—Ronald L. Frinks
*Attorney, Agent, or Firm*—Jeremiah J. Duggan; Alan H. Spencer

[57] ABSTRACT

A lens suitable for implantation in the eye is provided with iris clips formed of plastic filaments each having at least one of its ends fastened to the lens. Ends of the clips to be fastened are ferruled and beaded for secure and permanent affixation.

10 Claims, 6 Drawing Figures

IRIS CLIP ANCHORING MEANS FOR INTRAOCULAR LENSES

BACKGROUND OF THE INVENTION

1. Field of the Invention

This invention relates to improvements in ophthalmology and more particularly to improvements in artificial intraocular lenses (pseudophakoi) used for correction of aphakia and reestablishment of binocularity in aphakia.

2. Discussion of the Prior Art

Well-fixed and well-centered intraocular lens implants are known to produce stable retinal images with stable space localization and offer the best chance of re-establishment of binocularity in cases of aphakia.

Many techniques of lens implantation, including suturing to the ciliary muscle as disclosed in U.S. Pat. No. 3,711,870 and iris diaphragm fixation as disclosed in U.S. Pat. No. 3,673,616 have been used. The latter is considered to be a safe procedure giving good stability and the present invention deals with improvements in this general type of pseudophakos. More particularly, the invention relates to improvements in "iridocapsular" and/or "iris clipped" implants which have haptic sections respectively comprised of posterior and both posterior and anterior fastening elements all of which will be referred to as iris clips. The iris clips may be in the form of loops and/or struts of filament fastened to and extending away from the lenses.

Heretofore, iris clips have been formed of biologically inert metal wires which are at least in some respects, less than optimum in purpose. Even when formed of least dense of useful metals or alloys such loops and/or struts are relatively heavy in the eye, opaque and unaesthetic, less than optimally manipulatable before and/or during the surgical implantation and expensive both from the standpoint of precious metal cost and the intricacy of looped manufactured, not to mention the wire manufacturing operation itself.

An alternative to the use of metals for iris clips is that of using plastics, i.e. transparent or translucent filament or fiber formed of nylon, polymethyl methacrylate, polypropylene or other similarly chemically pure and biologically inert materials known to be available in the art. Fastening of these usually difficult to handle thin sections of plastics, however, has presented serious manufacturing problems. Staking, press fitting or interference fitting and other such attempts to fasten plastic iris cips in place are inherently difficult and tedious operations attended by high scrap yield and usually less than complete assurance against loosening or disconnection of parts during or following surgical implantation.

The use of adhesive which may avoid some of the problems of mechanical fixation procedures is, on the other hand, often turned away from for reasons of the possibilities of dangerous loosening and/or disasterous detachment of parts in the eye as a result of attack upon the bond or adhesive itself by ocular fluids.

It has been proposed in copending application Ser. No. 779,384, filed Mar. 21, 1977 that rigid ferruling be swaged, crimped or heat-sealed to ends of plastic iris clips and in turn anchored in apertured lenses by cold flow of the lens material around the ferruling.

While many of the drawbacks of older means and methods of anchoring iris clips are overcome by the invention of application Ser. No. 779,384, a disadvantage thereof is the difficulty of fitting a rigid ferrule having a blind hole onto an end of flexible iris clip material or vice versa. Another disadvantage is the tendency of plastic iris clip filament to experience stress release with time so that a squeeze fit at time of ferruling may not remain secure after stress release has occurred. Also, the close tolerence heretofore needed between diameter of filament and hole size in the ferrule render fabrication difficult, time consuming and costly.

In view of the foregoing, it is a principal object of this invention to overcome present difficulties and drawbacks attending the fixing of iris clips to lenses of pseudophakoi and more particularly to overcome the problems and difficulties currently experienced in providing these lenses with iris clips formed of plastic filaments.

A more specific object of the invention is to provide a novel and improved system and method for fixing plastic iris clips to lenses of pseudophakoi wherewith the attachment can be made simply, efficiently and economically especially with and added assurance of permanence throughout the expected useful life of the product.

Another object is to improve the locking of rigid ferruling to a less rigid iris clip filament while preserving the well known advantages of posterior blind hold anchoring which affords smooth and uninterrupted anterior lens surfaces.

Still another object is to provide for ease of fabrication and relaxation of dimensional tolerences in the ferruling of intraocular lens clips and to accomplish greater reproducibility of tight ferruling with minimal stress and avoidance of opportunity for subsequent stress corrosion.

Other objects and advantages of the invention will become apparent from the following description.

SUMMARY OF THE INVENTION

The foregoing objects and their corrolaries are accomplished by ferruling ends of plastic iris clips to be attached to lenses of pseudophakoi without need for staking, crimping, wedging or fusing to the plastic filament or fiber used to form the iris clips.

The present invention contemplates a system of applying a metal or rigid plastic ferrule, e.g. in the form of a ball, to a less rigid iris clip filament such as polypropylene by providing a thru hole in the ferrule. The clip material is passed completely through the ferrule and terminally beaded. An oversized filament or undersized hole is preferably used to insure tight fitting between filament and ferrule which, together with the filament beading, provides secure mechanical interlocking of the components. Disengagement due to stress release and/or plastic flow of filament material during use is prevented by a greater than heretofore area of contact between filament and ferrule which affords a correspondingly greater frictional holding force functioning together with beading of the filament to prevent its withdrawal.

Details of the invention will become more readily apparent from the following description when taken in conjunction with the accompanying drawings.

In the drawings

DESCRIPTION OF THE PREFERRED EMBODIMENTS

Figure 1:
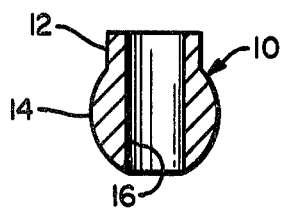
FIGS. 1, 2 and 3 depict means and method of ferruling iris clips according to the present invention. The ferruling being shown in cross-section for clarity of illustration.
Figure 2:
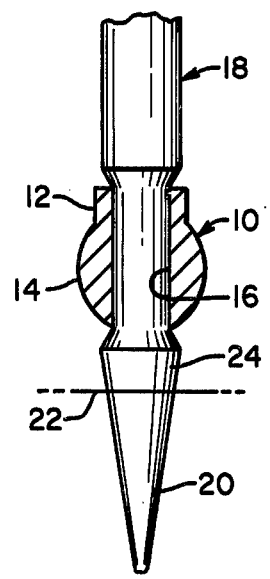
Figure 3:
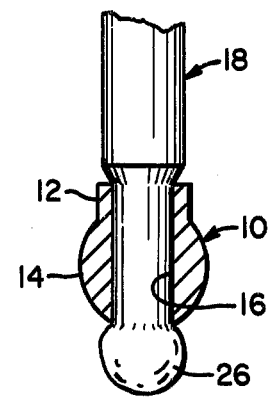
Figure 4:
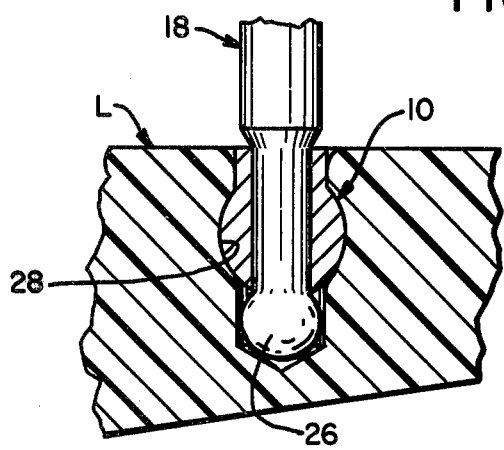
FIG. 4 is an illustration of an iris clip ferruled according to the invention and anchored within the material of an intraocularly implantable lens, the lens being shown in cross-section.
Figure 6:
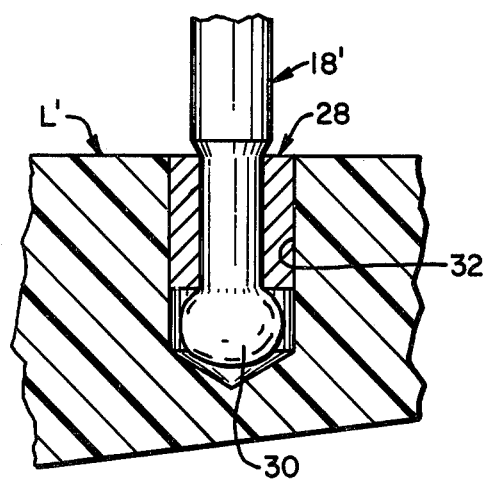
FIG. 6 is a view similar to FIG. 4 of another modification of the invention.

Means and method of ferruling iris clips according to the invention are illustrated in FIGS. 1-3 of the drawings and use of the invention is shown in FIGS. 4 and 6. Details of overall intraocular lens and iris clip shapes, sizes and/or other characteristics are omitted for reasons of such details not having particular pertinence to the present invention. Those interested in these details, however, may refer to one or more of U.S. Pat. Nos. 3,971,073; 3,996,626 and 4,012,823.

In matters of the present improvement in ferruling iris clip filaments, FIG. 1 illustrates ferrule 10 having the general shape of an apertured ball which may be formed of platinum, titanium, polymethyl methacrylate (PMMA), glass or any other suitable relatively rigid and biologically inert material.

In its presently illustrated shape, ferrule 10 is provided with neck 12 which affords a thru passageway 16 of a length greater than the diameter of ball portion 14. Neck 12 can be dispensed with if desired.

A procedure useful in forming ferrule 10 is to bead one end of a titanium or platinum wire with applied laser energy and shear slightly above the resulting ball portion to form neck 12. Passageway 16 may be drilled with laser energy and trued mechanically with tool drilling and/or reaming. For example, for ferruling a 0.006 inch diameter iris clip filament, one may use a 0.010 inch wire which is beaded to a diameter of 0.0105 inch and drilled to 0.006 inch maximum for producing passageway 16.

It is to be understood that the expression "wire" as used herein is not intended to restrict the invention to the use of metal ferrules. Present use of the word "wire" is intended to include filaments of hard plastics or other materials from which ferrules may be formed. Also it is pointed out that, while a laser may prove to be a useful tool in forming a metal ferrule as described above, the selection of type of laser and output energy level needed for particular beading, drilling and/or other operations will not be dealt with herein since such details are well within the realm of ordinary skill. In fact, simple sources of radiant energy may be used for beading plastic ferrules and/or machining operations alone may be used to produce metal or plastic ferrules according to the invention.

Applying ferrule 10 to an iris clip filament 18 of relative flexible material such as polypropylene is accomplished simply and efficiently by threading the filament completely through passageway 16 as illustrated in FIG. 2. Passageway 16 is preferably undersized as mentioned hereinabove to assure against subsequent loosening of the filament by latent stress relaxation.

The threading of filament 18 through ferrule 10 may be facilitated by tapering its leading end. Taper 20 (FIG. 2) may be formed, before threading, by heat-softening and stretching.

After threading as in FIG. 2 taper 20 is cut away, e.g. along line 22, and the remaining protrusion 24 of filament 18 is beaded as illustrated in FIG. 3. Bead 26 can be formed by applying heat to protrusion 24 of FIG. 2. Radiant energy or other sources of heat may be used according to the discretion of the artisan.

While protrusion 24 itself, i.e. without beading, may afford adequate mechanical locking of ferrule 10 as a result of its somewhat larger diameter than that of passageway 16, optimum security is accomplished by beading as just described. Beading also tends to relieve stresses in the filament material so that security of the connection is not adversely affected by subsequent stress corrosion or relaxation in the filament. Tolerances required between filament diameter and size of passageway 16 may also be relaxed. As opposed to prior art schemes of anchoring filaments in blind holes of ferrules, the present practice of threading completely through the ferrule permits the use of oversized filaments giving positive assurance of tight fit by plastic flow.

Use of the ferruled filament 18 of FIG. 3 is illustrated in FIG. 4.

Ferrule 10, being of larger diameter than the receiving opening 28 in lens L, is forced into opening 28 to cause a displacement of the material, e.g. PMMA, of the lens therearound for permanent locking of the ferrule to the lens. Iris clip filament 18 is, in turn, permanently securely locked in the ferrule.

Figure 5:
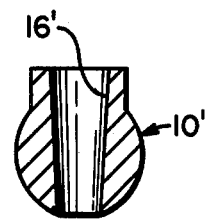
FIG. 5 is a cross-sectional view of a modification of the invention.

In FIG. 5 there is illustrated ferrule 10' having a thru passageway 16' which is tapered.

Another modification of ferruling is illustrated in FIG. 6 wherein ferrule 28 is cylindrical, i.e. without the above-described ball portion 14. Filament 18' is extended completely through ferrule 28 and provided with locking bead 30. Ferrule 28 may be friction fitted into opening 32 in lens L' and/or fused thereinplace. As in the cases of ferrules 10 and 10', ferrule 28 may be formed of the same material as lens L', e.g. PMMA or any other biologically inert plastic or metal.

Those skilled in the art will readily appreciate that there are various other modifications and adaptations of the precise form of the invention here shown and that the foregoing illustrations are not to be interpreted as restrictive beyond that necessitated by the following claims.

We claim:

1. An iris clip filament prepared for attachment to an intraocular lens comprising:
    a rigid ferrule having a passageway extending completely therethrough;
    said filament extending completely through the length of said passageway with protrusion therebeyond;
    the portion of said filament within said passageway being in frictional contact with said ferrule along said length of said passageway; and
    said protrusion being beaded to a diametral size greater than an adjacent diameter of said passageway.

2. An iris clip filament prepared for attachment to an intraocular lens according to claim 1 wherein said filament is formed of a flexible plastic material and said ferrule is formed of metal.

3. An iris clip filament prepared for attachment to an intraocular lens according to claim 1 wherein said filament is formed of a flexible plastic material and said ferrule is formed of a rigid plastic material.

4. An iris clip filament prepared for attachment to an intraocular lens according to claim 1 wherein said filament is compressed within said passageway.

5. An iris clip filament prepared for attachment to an intraocular lens according to claim 1 wherein said ferrule has a ball-shaped portion.

6. An iris clip filament prepared for attachment to an intraocular lens according to claim 5 wherein said ferrule includes a neck portion for extending the length of said passageway beyond the diametral dimension of said ball portion.

7. An iris clip filament prepared for attachment to an intraocular lens according to claim 1 wherein said ferrule is cylindrical in shape.

8. The intraocularly implantable system of a lens having an aperture and an iris clip filament anchored within said aperture wherein said system comprises:
a rigid ferrule, said ferrule being secured to said lens within said aperture and having a passageway extending completely therethrough in a direction generally parallel to said lens aperture, said filament extending completely through said passageway and protruding therebeyond, the portion of said filament within said passageway being in frictional contact with said ferrule within said passageway and said protrusion of said filament being beaded to a size substantially greater than an adjacent diameter of said passageway in said ferrule.

9. The intraocularly implantable system according to claim 8 wherein said ferrule has a ball-shaped portion.

10. The intraocularly implantable system of claim 8 wherein said ferrule is of cylindrical shape.

* * * * *